(12) United States Patent
Feygin

(10) Patent No.: US 6,846,461 B2
(45) Date of Patent: Jan. 25, 2005

(54) METHODS AND APPARATUS FOR IMPROVED FLUID CONTROL UTILIZING A U-VALVE EMPLOYING A FLOW-INTERRUPTION DEVICE

(75) Inventor: Ilya Feygin, Mountainside, NJ (US)

(73) Assignee: Pharmacopeia Drug Discovery, Inc., Cranbury, NJ (US)

( * ) Notice: Subject to any disclaimer, the term of this patent is extended or adjusted under 35 U.S.C. 154(b) by 37 days.

(21) Appl. No.: 09/873,087

(22) Filed: Jun. 1, 2001

(65) Prior Publication Data

US 2001/0026776 A1 Oct. 4, 2001

Related U.S. Application Data

(62) Division of application No. 09/283,126, filed on Mar. 31, 1999, now Pat. No. 6,254,835.

(51) Int. Cl.[7] ............................ B01L 11/00; G01N 1/10; F16K 11/00
(52) U.S. Cl. ........................ 422/103; 422/102; 422/99; 422/131; 137/388; 137/240
(58) Field of Search ................................ 137/388, 240, 137/192; 422/103, 131, 100, 98; 436/180

(56) References Cited

U.S. PATENT DOCUMENTS

| | | | | |
|---|---|---|---|---|
| 2,971,969 A | * | 2/1961 | Lobo | 556/190 |
| 3,167,395 A | * | 1/1965 | Spencer et al. | 422/131 |
| 3,990,853 A | * | 11/1976 | Godin | 422/100 |
| 4,016,864 A | * | 4/1977 | Sielaff et al. | 600/364 |
| 4,126,425 A | * | 11/1978 | Twigge-Molecey | 23/294 R |
| 4,211,254 A | * | 7/1980 | Dyal | 137/596.12 |
| 4,241,018 A | * | 12/1980 | Lang | 422/75 |
| 4,530,207 A | * | 7/1985 | Brannstrom | 60/39.464 |
| 4,567,021 A | * | 1/1986 | Sakagami | 422/102 |
| 4,792,432 A | * | 12/1988 | Ikonen | 422/72 |
| 4,798,221 A | * | 1/1989 | Crawford et al. | 137/119.04 |
| 5,405,585 A | * | 4/1995 | Coassin | 422/100 |
| 5,474,744 A | * | 12/1995 | Lerch | 422/100 |
| 5,565,324 A | * | 10/1996 | Still et al. | 435/6 |
| 5,663,046 A | * | 9/1997 | Baldwin et al. | 435/6 |
| 6,083,399 A | * | 7/2000 | Jameson et al. | 210/634 |
| 6,531,595 B2 | * | 3/2003 | Holderich et al. | 540/536 |

* cited by examiner

Primary Examiner—Jill Warden
Assistant Examiner—Brian R. Gordon

(57) ABSTRACT

A U-valve apparatus including a bidirectional check valve for controlling the flow of liquid from a vessel while preventing inadvertent discharge from the vessel. The check valve allows passage of a fluid such a gas into the vessel, for purposes of agitating the liquid or for other purposes, and also permits the evacuation of the liquid from the vessel. The U-valve apparatus is advantageously included in a universal fluid exchange device including upper and lower reaction vessel supports which include pressure sealed injection and evacuation ports for each supported reaction vessel. Reaction vessels matingly engage through the injection and evacuation ports with fittings which are connected through flexible tubing to respective supplying and receiving vessels. Each of one or more reaction vessels may suitably be connected by a U-valve apparatus including a check valve to a corresponding receiving vessel. The reaction vessels or fittings are moved into position, as required, so that reactants may be directly supplied from supplying vessels in the order and amount desired without operation of valves that can become contaminated, and so that the reaction vessels may dispel their contents into the appropriate receiving vessels. The system may be highly advantageous in applications such as combinatorial chemistry where myriad combinations of chemicals, solvents and reagents are employed.

18 Claims, 11 Drawing Sheets

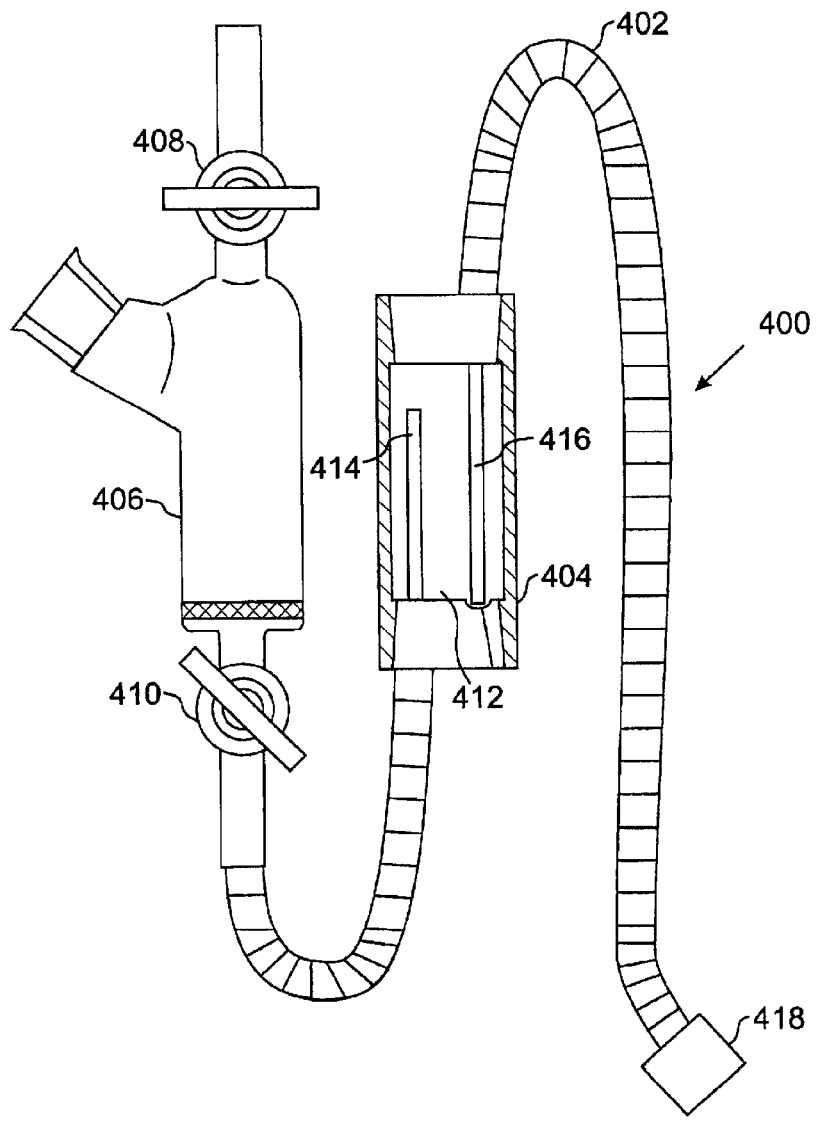
FIG. 4
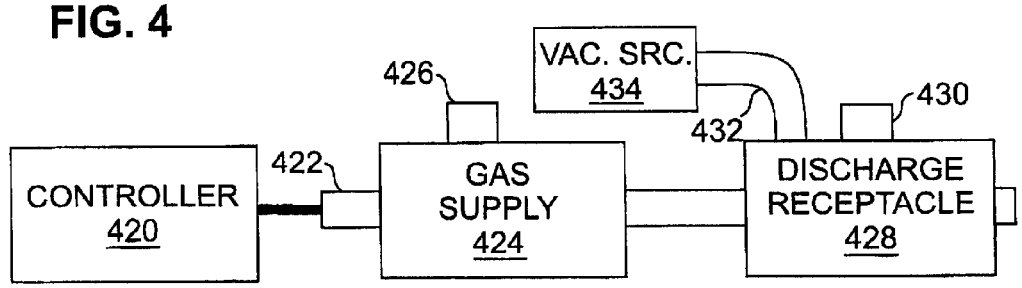

METHODS AND APPARATUS FOR IMPROVED FLUID CONTROL UTILIZING A U-VALVE EMPLOYING A FLOW-INTERRUPTION DEVICE

This is a division of application Ser. No. 09/283,126 filed on Mar. 31, 1999 now U.S. Pat. No. 6,254,835.

CROSS-REFERENCE TO RELATED APPLICATION

U.S. application Ser. No. 08/872,097 filed Jun. 10, 1997 and assigned to the assignee of the present invention addresses related subject matter and is incorporated herein in its entirety.

BACKGROUND OF THE INVENTION

1. Field of the Invention

The present invention is related generally to control of liquid flow from a vessel. More particularly, the invention relates to a bi-directional check valve for use in conjunction with a U-valve for preventing inadvertent self discharge of a liquid from a vessel.

2. Description of the Related Art

One commonly used technique for the control of discharge while reducing the need for complex valve systems is a U-valve arrangement. It is advantageous to provide a U-shaped tube, commonly referred to as a U-valve, at a bottom port of a vessel, in order to prevent the self discharge of liquid from an open bottom port of the vessel. Under ordinary circumstances, the U-shaped tube allows the liquid from the vessel to enter the tube to a level which does not exceed the level of the liquid in the vessel. This arrangement allows the convenient maintenance of equilibrium of liquid level in the vessel, without requiring that a valve at the bottom of the vessel remain closed. It is possible, however, to use such a U-shaped tube to discharge liquid from the vessel by applying a negative pressure to the tube. It is also possible to use the U-shaped tube to purge the vessel by directed gas under positive pressure from the output end of the tube.

A U-valve works reliably with large tubing inner dimensions (IDs), and under room temperature conditions; however, a U-valve based on small ID tubing and operated with sufficiently hot liquids may cause undesired discharge of the contents of a vessel through the U-shaped tubing. This occurs because of increased pressure inside the vessel and the origination of gas bubbles in the fluid under higher temperature conditions. The formation of gas bubbles can cause the level of liquid in the vessel to rise above the level of liquid in the U-shaped tube, resulting in a siphoning effect, which can cause a complete discharge of the liquid from the vessel. Smaller ID tubing may exhibit capillary action, which increases the likelihood of siphoning. Thus, in many cases the U-valve arrangement requires the use of an additional valve or a plurality of additional valves, causing additional expense and increasing the complexity of the system.

The importance of simplicity in chemical systems is readily apparent when considered in the context of parallel chemical reactions. The ability to appropriately manipulate reaction vessels for a plurality of parallel chemical reactions and to provide and evacuate fluids from such vessels is becoming increasingly important. As the number of desired chemical reactions increases, manual or simple mechanical arrangements become impractical. By way of example, combinatorial chemical synthesis permits the production of very large numbers of small molecule chemical compounds which may, for example, be tested for biological activity.

Certain combinatorial synthesis methods employ polymeric resin beads as solid phase substrates upon which the small molecule compounds are formed. In these methods, sometimes referred to as the "mix and split", and "direct divide" methods, a sample of beads is divided among several reaction vessels and a different reaction is performed in each vessel. The beads from all the vessels are then pooled and/or redivided into a second set of vessels, each of which now contains approximately equal numbers of beads carrying the products of the first set of reactions. When a second reaction is performed, each of the products of the first set of reactions acts as a substrate for a new set of reactions which produce all the possible combinations of reaction products.

The mix and split combinatorial chemical synthesis method is discussed in greater detail in, M. A. Gallop, R. W. Barrett, W. J. Dower, S. P. A. Fodor and E. M. Gordon, Applications of Combinatorial Technologies to Drug Discovery, 1. Background and Peptide Combinatorial Libraries, Journal of Medical Chemistry 1994, Vol. 37, pp. 1233–1251; E. M Gordon, R. W. Barrett, W. J. Dower, S. P. A. Fodor and M. A. Gallop, Applications of Combinatorial Technologies to Drug Discovery, 2. Combinatorial Organic Synthesis, Library Screening Strategies and Future Directions, Journal of Medical Chemistry 1994, Vol. 37, pp.1385–1401, M. R. Pavia, T. K. Sawyer, W. H. Moos, The Generation of Molecular Diversity, Bioorg. Med. Chem. Lett. 1993, Vol. 3, pp. 387–396 and M. C. Desai, R. N. Zuckerman and W. H. Moos, Recent Advances in the Generation of Chemical Diversity Libraries, Drug Dev. Res. 1994, Vol. 33, pp. 174–188 which are hereby incorporated by reference. See also, U.S. Pat. No. 5,565,324 which is also hereby incorporated by reference. The direct divide method is described in greater detail in U.S. Pat. No. 5,663,046 incorporated by reference herein in its entirety.

By providing an extremely large library of chemical compounds for testing, combinatorial chemical synthesis facilitates the development of compounds which may be used to develop new drugs for treating a wide range of diseases. Rather than painstakingly manually synthesizing chemicals one at a time and individually testing them for biological activity with, for example, an enzyme involved in heart disease, or a cell receptor involved in fighting cancer, many chemicals can be developed and tested in parallel, greatly accelerating the drug development process and, hopefully, leading to major advances in the treatment and prevention of disease.

Unfortunately, the task of simultaneously synthesizing a large number of compounds can involve complex, unwieldy processes and equipment. Generally, reagents and solvents must be added to reaction vessels in precisely timed sequences. Additionally, the temperature of each reaction vessel must often be well-defined and a specific temperature profile may be required for optimal reaction. Typically, the contents of each reaction vessel should be stirred or mixed in order to ensure the proper distribution of reactants.

One conventional approach to delivering fluids to reaction vessels relies upon a labyrinthine plumbing system which routes solvents, reactants and reagents to various reaction vessels through tubes selected by a complex valving system which may be under computer control. A similar system is required to remove the reaction products from vessels. Not only is such a system complex and expensive, it also presents major maintenance, reliability and contamination problems.

For example, all the tube material and the valves which direct flow among the tubes must be maintained on a regular basis. The valve materials may be corroded or otherwise damaged by contact with the reagents, solvents or reaction products and consequently must be vigilantly maintained in order to prevent cross-contamination. Even if the valves and tubes are well-maintained, in light of the diverse range of chemicals that may be involved, there is still a very real threat of corrosion and cross-contamination. Additionally, controlling the timing, mixing, and heating of reactants within such a complex system is a formidable task and, with conventional mixing systems, the beads which provide reaction surfaces often are undesirably ground up to some extent against the bottom of the reaction vessel.

In order to reduce the complex plumbing of valve and tube systems, some systems rely upon robotic arms to deliver reagents into reaction vessels under program control. Although the complexity of the plumbing system is greatly reduced in these systems, the robotic system is highly complex and subject to its own problems. Regular maintenance is required on such systems, spills are an inherent hazard, contamination remains a problem, and it may be difficult to control the temperature of, and to provide proper agitation for, reactants.

Such systems typically include complex valving arrangements for flow control, increasing the cost and complexity of such systems and processes.

There exists, therefore, a need in the art for a simple arrangement to prevent the inadvertent self-discharge of liquid through a U-valve, while allowing gases and liquids to pass through the U-valve when desired, and which can be used in the context of a parallel chemical reaction environment in which many valves may be employed.

SUMMARY OF THE INVENTION

A U-valve apparatus according to one aspect of the present invention includes a bi-directional check valve placed in a U-valve leading out of a discharge port of a vessels. The check valve includes a first channel including a first valve adapted to block liquid flow out of the vessel and through the U-valve. The first valve is adapted to allow a flow of a gas through the U-valve and into the vessel. The check valve also advantageously includes a second channel having a second valve adapted to be in one of an open position or a closed position. The second valve is adapted to block liquid flow in the direction out of the vessel through the U-valve when the second valve is in the closed position. When the second valve is in the open position, the second valve allows liquid flow out of the vessel through the U-valve. The second valve is adapted to be opened by an application of a negative pressure exerted through the U-valve on the second valve.

An alternative U-valve apparatus according to another aspect of the present invention includes a flow interruption device included in a U-valve. The flow interruption device includes a sealed chamber with an inlet tube and an outlet tube. A liquid flows into the chamber at the inlet until the level of liquid in the chamber reaches the level of liquid in the vessel. Because of the interruption of the liquid flow provided by the flow interruption device, the likelihood of siphoning from the vessel through the U-valve is greatly reduced. It is possible, however, to deliberately evacuate the vessel by exerting a negative pressure on the U-valve, creating a negative pressure and tending to draw liquid out of the chamber through the outlet.

A U-valve apparatus according to the present invention may advantageously be used in conjunction with a universal fluid exchange apparatus for controlling the manipulation of one or more reaction vessels. Such a fluid exchanger may suitably be employed in combinatorial chemical synthesis reaction systems which are simple, low cost and highly reliable, but will be applicable in a wide variety of contexts. One suitable fluid exchanger is described in U.S. patent application Ser. No. 08/872,097 filed Jun. 10, 1997 which is incorporated by reference herein in its entirety. A universal fluid exchanger suitable for use with a U-valve apparatus according to the present invention may reduce the likelihood of spills and of cross contamination, provide for the effective individual heating of reaction vessels, and supply effective agitation of reactants without substantially grinding up internal particles, such as the microscopic beads which support the chemical compounds in combinatorial chemical synthesis, thereby increasing the yield of the synthesis. The U-valve apparatus of the present invention prevents undesired discharge from each of the reaction vessels, while allowing convenient entry of gas for agitation, and evacuation from the reaction vessel.

A fluid exchange system including a check valve according to the present invention may comprise upper and lower reaction vessel supports which include pressure sealed injection and evacuation ports for each supported reaction vessel. Reaction vessels matingly engage through the injection and evacuation ports with fittings which are connected through flexible tubing to respective supplying and receiving vessels. The reaction vessels, or fittings, are moved into position, as required, so that the reaction vessel may be supplied with reactants from supplying vessels in the order and amount desired and so that the reaction vessels may provide their contents to the appropriate receiving vessels. By moving the vessels, fluids may be supplied through dedicated supply lines which will not become contaminated as they will only deliver a single type of fluid.

A more complete understanding of the present invention, as well as further features and advantages of the invention, will be apparent from the following Detailed Description and the accompanying drawings.

BRIEF DESCRIPTION OF THE DRAWINGS

FIG. 4 illustrates a U-valve apparatus employing a flow interruption device, according to the present invention.

DETAILED DESCRIPTION

Figure 1:
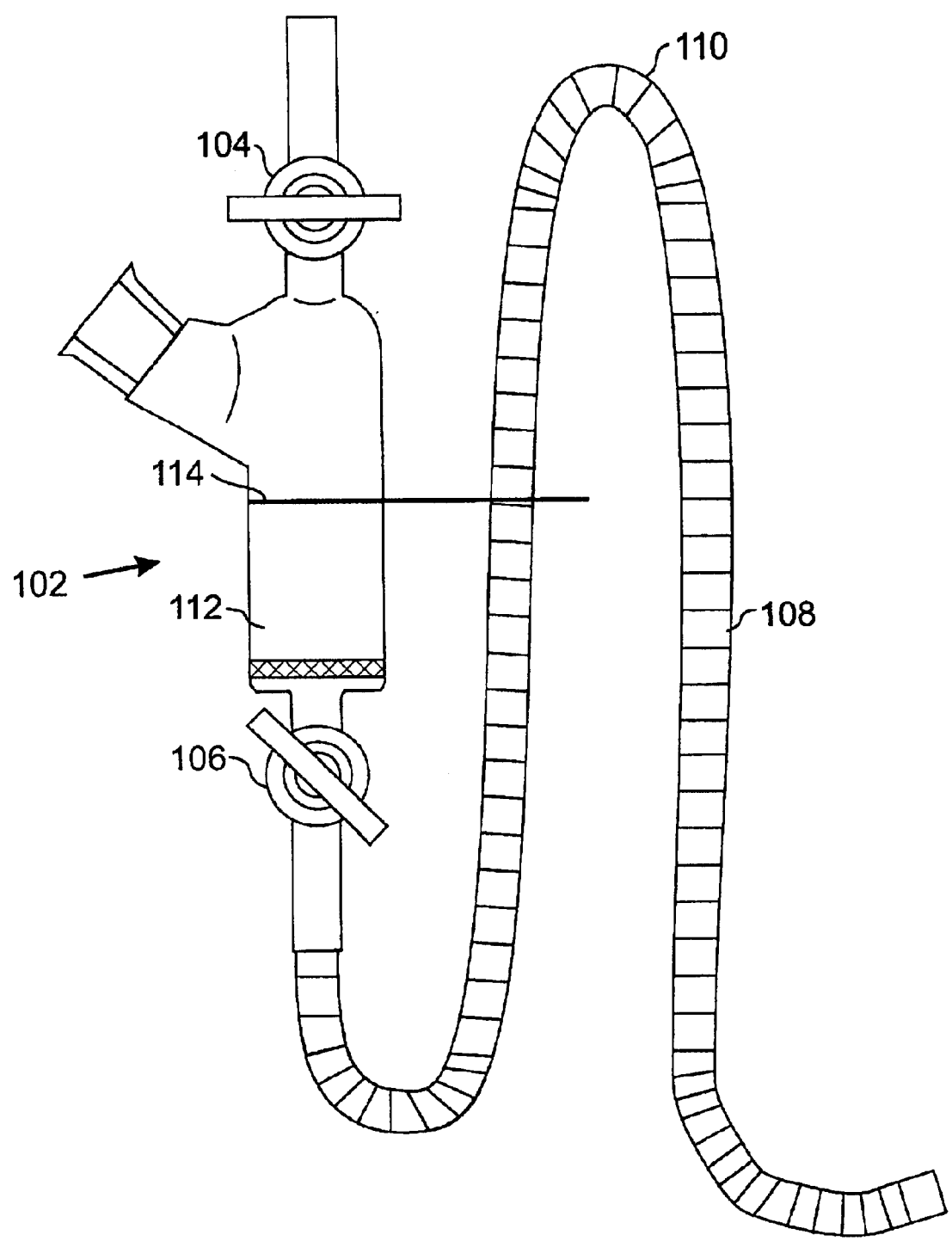
FIG. 1 illustrates a reaction vessel connected to a U-valve.

FIG. 1 illustrates a reaction vessel 102 having top and bottom stopcocks 104 and 106, connected to a U-valve 108. The U-valve 108 has an apex or highest point 110. The reaction vessel 102 contains a liquid 112 having a level 114. Normally, when the bottom stopcock 106 is open and the U-valve 108 is in the closed position, that is, when the apex 110 is above the level 114, the liquid 112 flows into the U-valve 108 until the liquid 112 in the U-valve 108 reaches the level 114. In some cases however, such as with the use of small ID tubing for the U-valve 108, or when the liquid 112 is sufficiently hot, the liquid 112 may be forced past the level 114 and past the apex 110 of the U-valve 108, and then tend to flow continuously out of the vessel 102 through the U-valve 108.

Figure 2:
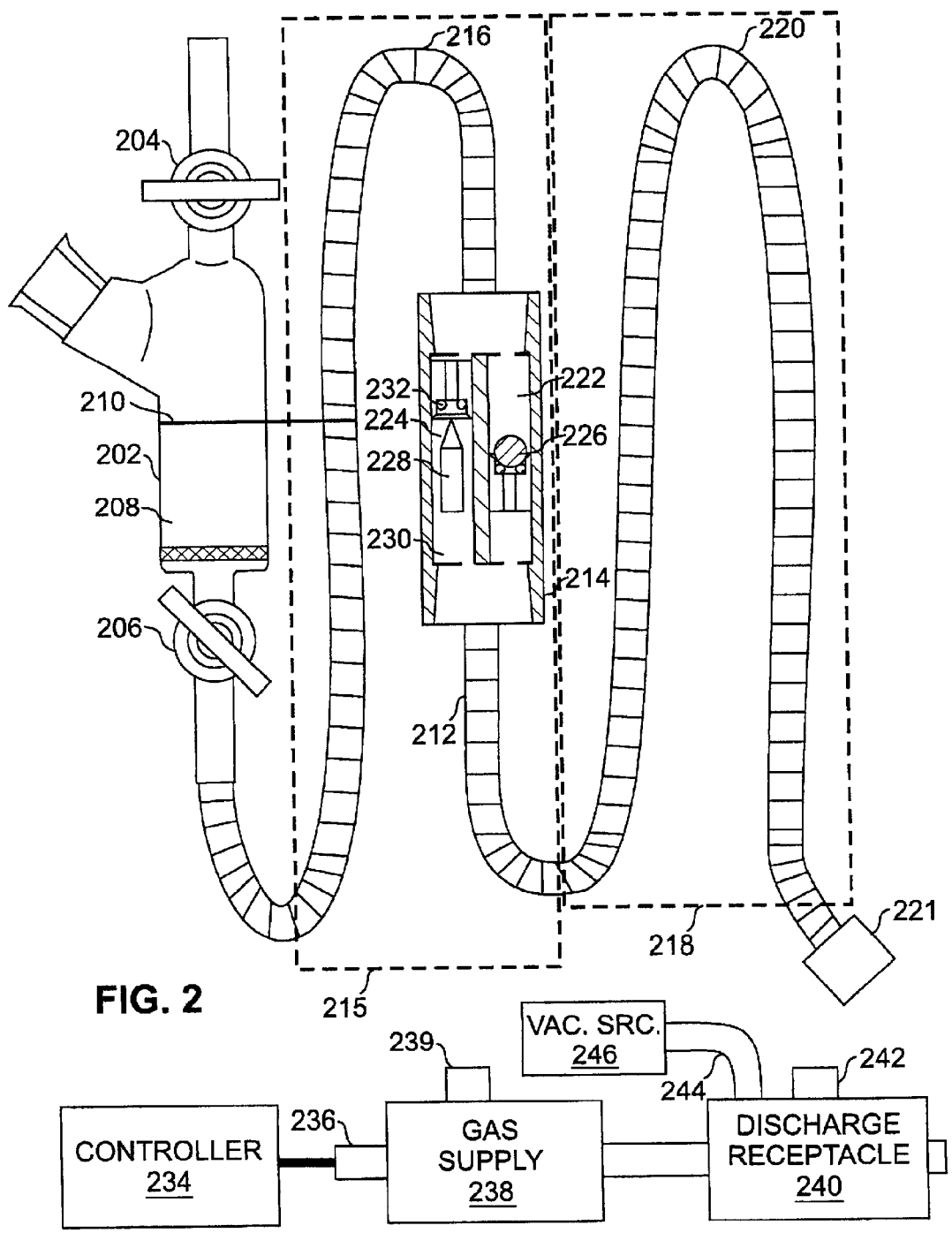
FIG. 2 illustrates a reaction vessel connected to a U-valve apparatus employing a bidirectional check valve, according to the present invention.

FIG. 2 illustrates a reaction vessel 202 having top and bottom stopcocks 204 and 206, respectively. The reaction vessel 202 contains a liquid 208 having a level 210. Also shown is a U-valve 212 according to the present invention, containing a bi-directional check valve 214 according to the present invention. The U-valve 212 is modified from that described above in connection with FIG. 1 with the U-valve 212 including a first section 215 having a first apex 216, and a second section 218. The second section 218 includes a second apex 220. A connection fitting 221 is attached to the U-valve. A controller 234 controls operation of a carousel 236, which contains a gas supply 238 and a discharge receptacle 240, the gas supply 238 and the discharge receptacle 240 being alternatively connectable to the second section 218 of the U-valve 212. The gas supply 238 has a gas supply port 239 for connection to the U-valve 212. The gas supply port 239 is adapted to mate with the connection fitting 221. The discharge receptacle 240 has a discharge receptacle entry port 242 for connection to the U-valve 212 and a vacuum port 244, connectable to a vacuum source 246 for creating a negative pressure within the discharge receptacle 240 and the U-valve 212. The discharge receptacle entry port 242 is adapted to mate with the connection fitting 221.

Normally, when the bottom stopcock 206 is open and the U-valve 212 is in the closed position, the liquid 208 flows into the U-valve 212 until the liquid 208 in the U-valve 212 reaches the level 210. As noted above however, with the use of small ID tubing for the U-valve 212 or when the liquid 208 is sufficiently hot, the liquid 208 may be forced past the level 210 and past the first apex 216. Once this happens, the liquid 208, if not stopped, will tend to flow out of the vessel 202 through the U-valve 212. To prevent this, the U-valve 212 contains the bi-directional check valve 214 and the second section 218 according to the present invention. The bidirectional check valve 214 includes first and second parallel independent channels 222 and 224. The first channel 222 is blocked in the direction of liquid evacuation by a ball valve 226 which uses gravity to prevent the flow of liquid. The ball valve 226 is normally held closed by gravity, and when the liquid 208 flows into the first channel 222, the weight of the liquid 208 increases the pressure on the ball valve 226, forming a tighter seal. However, the ball valve 226 allows flow of a gas in a direction opposite to the flow of liquid, that is, into the reaction vessel 202. If it is desired to introduce a gas into the vessel, for agitation of the liquid or for other purposes, the controller 234 may direct attachment of the gas supply 238 to the second section 218 of the U-valve 212, and then direct release of gas into the vessel 204 through the U-valve 212. When the pressurized gas is introduced into the first channel 222 in the direction opposite to the flow of liquid, the ball valve 226 is forced open, admitting the gas into the first channel 222, and allowing the gas entry into the reaction vessel 202, so that the reaction vessel 202 may be evacuated through the bottom stopcock 206, or so that the liquid may be agitated by the action of the gas.

The second channel 224, adjacent to the first channel 222, is equipped with a floating valve 228 which also prevents escape of the liquid 208. The floating valve 228 is positioned above a reservoir 230. If the liquid 230 enters the second channel 224 and flows onward into the second section 218 of the U-valve 212, and the level of liquid in the second section 218 of the U-valve 210 reaches the level 210 of liquid in the reaction vessel 202, the liquid 208 backs up in the reservoir 230, causing the floating valve 228 to float until the floating valve 228 seals an orifice 232. The check valve 214 prevents more than a minimum amount of the liquid 208 from escaping the vessel 202 before the reservoir 230 fills with liquid, closing the floating valve 228. When it is desired to evacuate the vessel 204, the controller 234 directs connection of the discharge receptacle entry port 242 of the discharge receptacle 240 to the second section 218 of the U-valve 212, and directs the vacuum source 246 to supply a vacuum to the vacuum port 244, in order to apply a negative pressure to the second section 218 of the U-valve 212, causing the floating valve 228 to be drawn downward, opening the orifice 232 and allowing the escape of the liquid 208 into the discharge receptacle 240.

Figure 3:
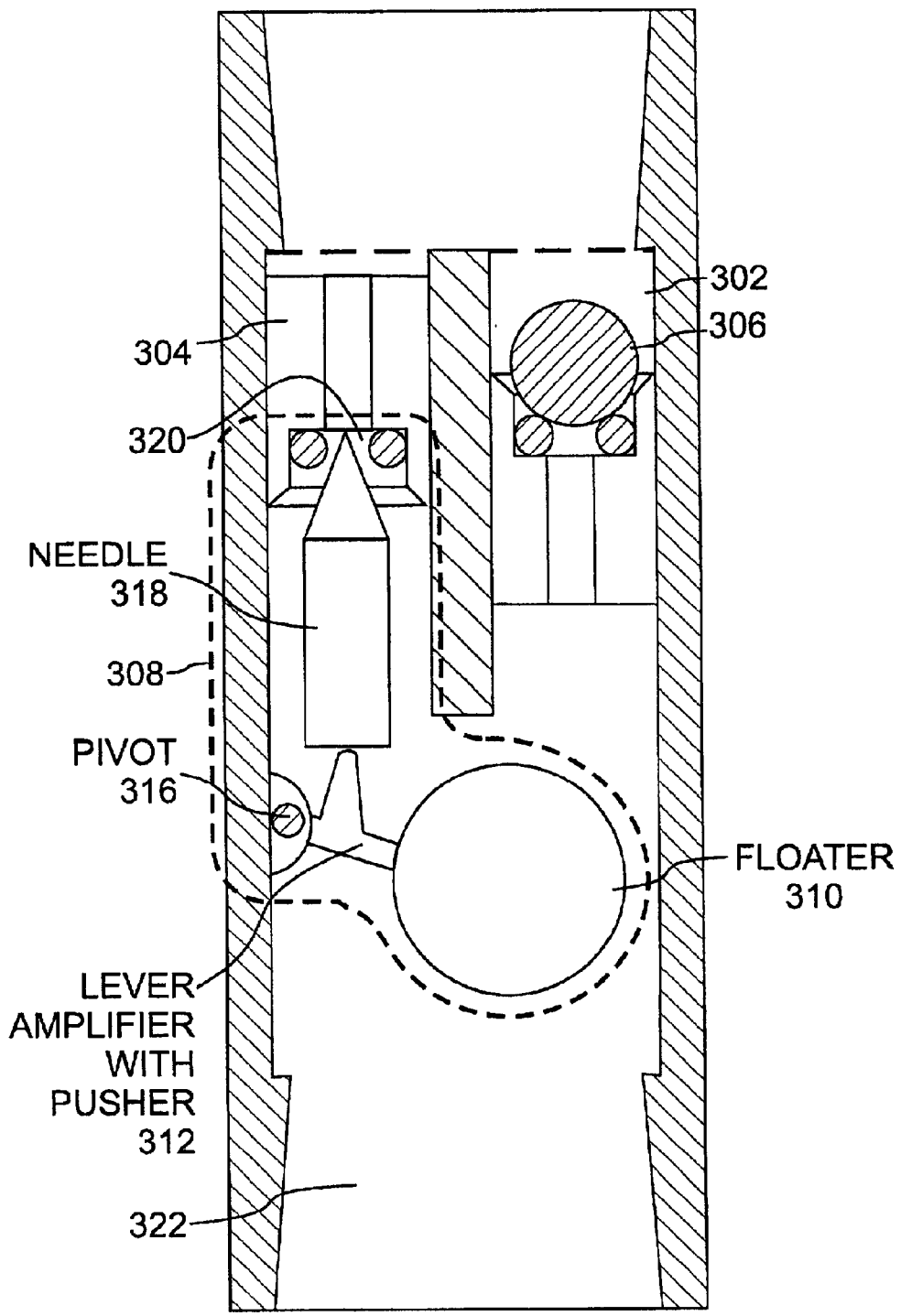
FIG. 3 illustrates an alternative bidirectional check valve according to the present invention.

FIG. 3 illustrates a check valve 300 according to an alternative aspect of the present invention. The check valve 300 may be substituted for the check valve 214 of FIG. 2. The check valve 300 includes a first channel 302 and a second channel 304. The first channel 302 includes a ball valve 306 similar to the ball valve 226 of FIG. 2. The second channel 304 is adapted to be opened and closed by a floating valve assembly 308 which performs the same function as the floating valve 228 of FIG. 2. The floating valve assembly 308 includes a floater 310 which is attached to a lever amplifier 312. The lever amplifier includes a pusher 314. The lever amplifier 312 is attached to a pivot 316 which serves as a fulcrum for the lever amplifier 312. The pusher 314 supports a needle 318, which operates to seal and open an orifice 320 similar to the orifice 232 of FIG. 2. The check valve 300 also includes a reservoir 322. When the reservoir 322 is empty or only partially filled, the floater 312 is in a lowered position, so that the needle 318 is lowered and the orifice 320 is open. As the reservoir 322 fills, the floater 310 rises, raising the lever amplifier 312 and in turn raising the needle 318, so that eventually the needle 318 seals the orifice 320. The floater 310 is typically larger than the floating valve 228 of FIG. 2, for a bidirectional valve 300 of a similar size to a bidirectional valve 214 of FIG. 2. Moreover, the action of the lever amplifier 312 about the pivot 316 amplifies the force exerted on the needle 318.

FIG. 4 illustrates a U-valve apparatus 400 according to an alternative aspect of the present invention. The U-valve apparatus 400 includes a U-valve 402 including a flow interruption device 404. The U-valve apparatus is attached to a reaction vessel 406, which includes top 408 and bottom 410 stopcocks. The flow interruption chamber device 404 includes a fully enclosed and preferably sealed chamber 412, which includes inlet 414 and outlet 416 tubes. The presence of the flow interruption device 404 prevents siphoning through the U-valve 402 by interrupting any flow of liquid from the U-valve 402. The flow interruption device 404 allows purging of the reaction vessel 406, or agitation of liquid within the reaction vessel 406, by allowing passage of gas into the vessel 406. Additionally, the flow interruption device 404 allows the vessel 406 to be evacuated through suction applied to the U-valve 402. The suction creates a negative pressure whose transmission is not prevented by the flow interruption device 404. Application of suction will draw liquid into the chamber 412 through the inlet tube 414, filling the chamber 412, and then drawing liquid out of the chamber 412 through the outlet tube 416. The U-valve is preferably fitted with a connection fitting 418 for connection to a discharge receptacle similar to the discharge vessel 240 of FIG. 2 or to a gas supply similar to the gas supply 238 of FIG. 2.

In a presently preferred embodiment, one or more U-valve apparatuses according to the present invention are employed in a universal fluid exchanger. The universal fluid exchanger is preferably simple, low cost and reliable, and prevents the unintended discharge of liquids without the need for complicated valve systems. By comparison with conventional systems employed in combinatorial chemical syntheses, parallel chemical syntheses, and the like, it reduces the likelihood of spills and of cross contamination, allows effective heating of reaction vessels, and supplies effective agitation of reactants without grinding solid phase materials in the vessels, such as the microscopic beads which support the chemical compounds in combinatorial chemical reactions.

In this preferred embodiment, a universal fluid exchanger may suitably comprise upper and lower reaction vessel supports which include pressure sealed injection and evacuation ports for each supported reaction vessel. Reaction vessels matingly engage through the injection and evacuation ports with fittings which are connected through flexible tubing to respective supplying and receiving vessels. One or more of the flexible tubes are in the form of U-valves including a bidirectional check valve according to the present invention. In the presently preferred embodiments, these flexible tubes deliver fluids directly from a supply vessel to a reaction vessel without intervening valves. One suitable way of controlling this delivery of fluids is by pressurizing the supply vessels and controllably adjusting the pressure to control fluid delivery. It will be recognized that a variety of other techniques might also be employed.

The reaction vessels, or fittings, are preferably moved into position, as required, so that the reaction vessel may be supplied with reactants from the appropriate supplying vessel in the order and amount desired. As each delivery tube is dedicated to an associated supplying vessel, the risk of cross contamination is eliminated. Similarly, movement of the fittings or vessels permits proper alignment of the reaction vessels for drainage of the contents of the reaction vessels into receiving vessels.

Figure 5:
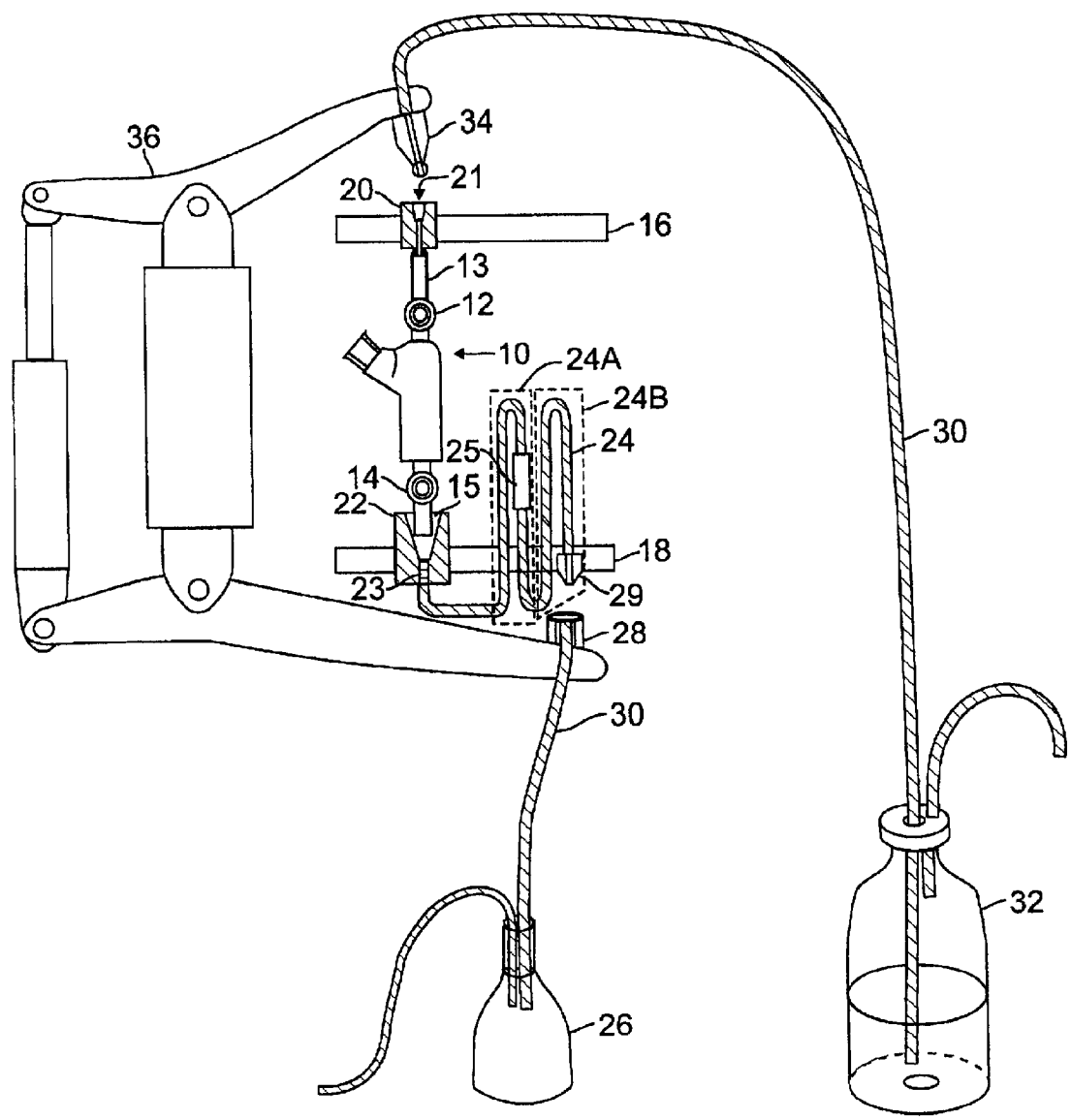
FIG. 5 illustrates the basic components of a universal fluid exchanger suitably employing a U-valve apparatus utilizing a bidirectional check valve, in accordance with the present invention.

FIG. 5 illustrates an embodiment of a universal fluid exchanger suitably including a reaction vessel 10. While a single reaction vessel 10 is shown, it will be recognized that a plurality of vessels will typically be employed as discussed further below. A presently preferred vessel for use as the vessel 10 is described in greater detail in "A Solid Phase Synthesis Reaction Vessel and Method of Using Same," U.S. Ser. No. 08/337,268, filed Sep. 29, 1995 and which is incorporated by reference herein. The vessel 10 may have top 12 and bottom 14 stopcocks, respectively, which are preferably made of TEFLON®. Top and bottom glass tubes 13 and 15 of vessel 10 may be simply clamped into mounts 20 and 22, alternatively, spring loaded, or other fittings may be employed in the top and bottom. Chemically resistant O-rings, disposed at the ends of tubes 13 and 15 might also be used to facilitate the insertion or removal of the vessel 10. Respective top 16 and bottom 18 reaction vessel supports accommodate the reaction vessel 10. Injection 21 and evacuation 23 ports associated respectively with supports 16 and 18, communicate with vessel 10 through mounts 20 and 22, respectively. Ports 21 and 23 are preferably composed of a resilient material such as TEFLON® for pressure-sealed access to the reaction vessel 10.

Figure 6B:
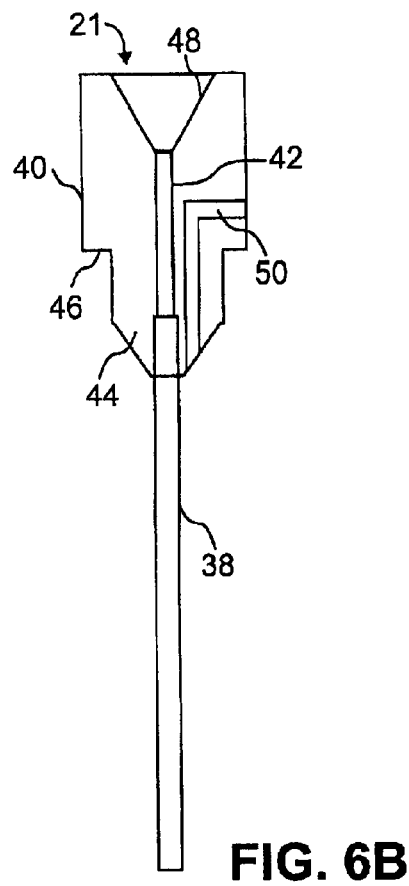
FIGS. 6B and 6C are sectional views of suitable reaction vessel injection and evacuation ports for the reaction vessel of FIG. 6A.
Figure 6C:
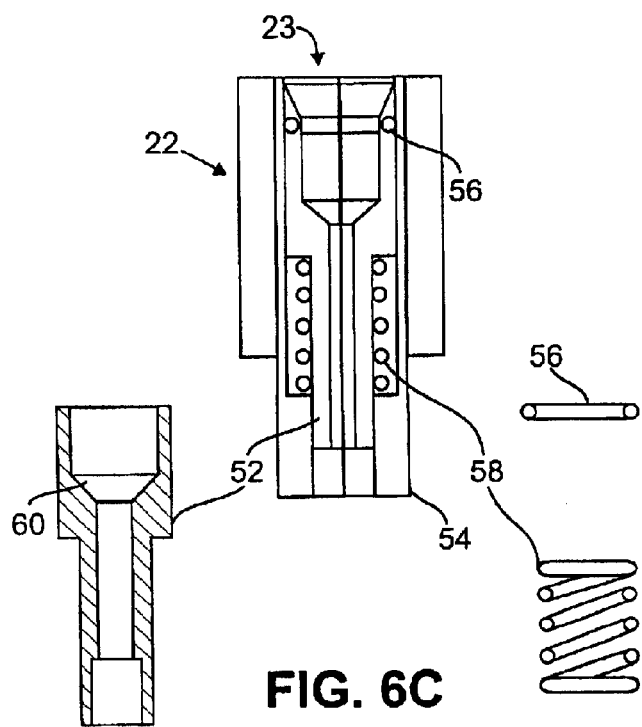

As described in greater detail in relation to the discussion of FIGS. 6B and 6C, the presently preferred injection port 21 includes a through fitting and top glass vessel tube 13, and the presently preferred evacuation port 23 includes a spring-loaded bottom through fitting and bottom glass vessel tube 15. In combination, the spring loaded through fitting of the evacuation port 23 and the through fitting of the injection port 21 permit easy removal and replacement of the reaction vessel 10.

Each reaction vessel 10 preferably has an associated U-valve 24 composed of flexible non-reactive tubing such as standard commercially available TEFLON® tubing, which selectively shuts or opens the flow of materials from the reaction vessel 10 through the evacuation port 23 to a receiving vessel 26 which is connected to an evacuation fitting 28 through flexible tubing 30. The U-valve 24 includes a bidirectional check valve 25 according to the present invention, similar to the bidirectional check valve 214 of FIG. 2. The U-valve 24 is shut when in a raised vertical position and open when in it is placed in a horizontal position and the bidirectional check valve 25 is opened through the application of negative pressure as discussed above in connection with the discussion of FIG. 2. As discussed in connection with FIG. 2, the bidirectional check valve 25 prevents inadvertent discharge from the reaction vessel 10, but allows introduction of gas into the reaction vessel 10 for agitation of a liquid contained in the reaction vessel 10, or evacuation of the liquid from the reaction vessel 10 through the application of a negative pressure to the U-valve 24. As discussed in connection with the U-valve of FIG. 2, the U-valve 24 includes first and second sections 24A and 24B to provide proper operation of the check valve 25. As the evacuation fitting 28 matingly engages with a through fitting 29 that is located on the vessel support 18 and is connected to the U-valve 24. A supplying vessel 32 is connected through flexible tubing 30 to an injection fitting 34 which matingly engages the injection port 21. A locking actuator 36 is employed to mate or clamp injection fitting 34 with injection port 21 and evacuation fitting 28 with through fitting 29. If desired, a bidirectional check valve similar to the check valve 300 of FIG. 3 may be substituted for the check valve 25. For an alternative configuration, the U-valve 24 and the check valve 25 may be replaced by a U-valve and flow interruption device similar to the U-valve 402 and flow interruption device 404 of FIG. 4.

Figure 6A:
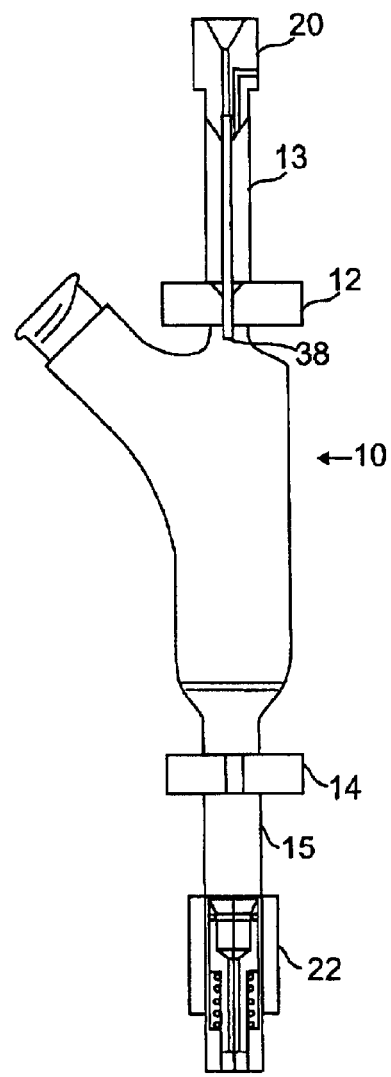
FIG. 6A illustrates a suitable reaction vessel for use in conjunction with a U-valve apparatus employing a bidirectional check valve, according to the present invention.

FIG. 6A illustrates a presently preferred reaction vessel 10 in greater detail. The top stopcock 12 is preferably composed of a resilient material, such as TEFLON®, which permits penetration by a needle 38 that forms a part of the injection fitting 20, and may be operated by hand. The bottom stopcock 14 is also preferably composed of TEFLON® and operated by hand. With the bottom stopcock 14 open and U-valve 24 in its open horizontal position, the vessel 10 may be evacuated by suction from a receiving vessel, such as the vessel 26.

The injection fitting 20 is illustrated in greater detail in FIG. 6B. A top fitting seal 40 is preferably composed of TEFLON®. The seal 40 includes a channel 42 which provides a path through the seal 40 to the needle 38. In the preferred embodiment, the needle 38 may be fitted with a sprayer attachment with which to wash the inner surfaces of the vessel 10. A tapered end 44 fits within the inside diameter of the top vessel glass tube 13 and an annular shoulder 46 abuts the top of the glass tube 13. A tapered inlet 48 accepts the injection fitting 34. The seal 40 also includes a bleeding channel 50 which may be utilized to connect the interior of the vessel 10 to the ambient environment and relieves excess pressure within the vessel 10 during the filling process or as otherwise desired during system operation.

FIG. 6C illustrates the spring-loaded evacuation fitting 22 in greater detail. An inner sleeve 52 rests within an outer sleeve 54. An O-ring 56 is affixed to the top of the inner sleeve 52 and seals against the outside diameter of the vessel's bottom glass tube 15. A spring 58 is located between the inner sleeve 52 and outer sleeve 54 and provides constant pressure between the tapered bottom of the glass tube 15 and a tapered inlet 60 of the inner sleeve 52. In this manner, both the inner sleeve 52 and O-ring 56 seal the fitting 22 against the glass tube 15. Additionally, since the fitting 22 is spring-loaded, the vessel 10 may be easily removed and replaced without leakage.

Figure 7A:
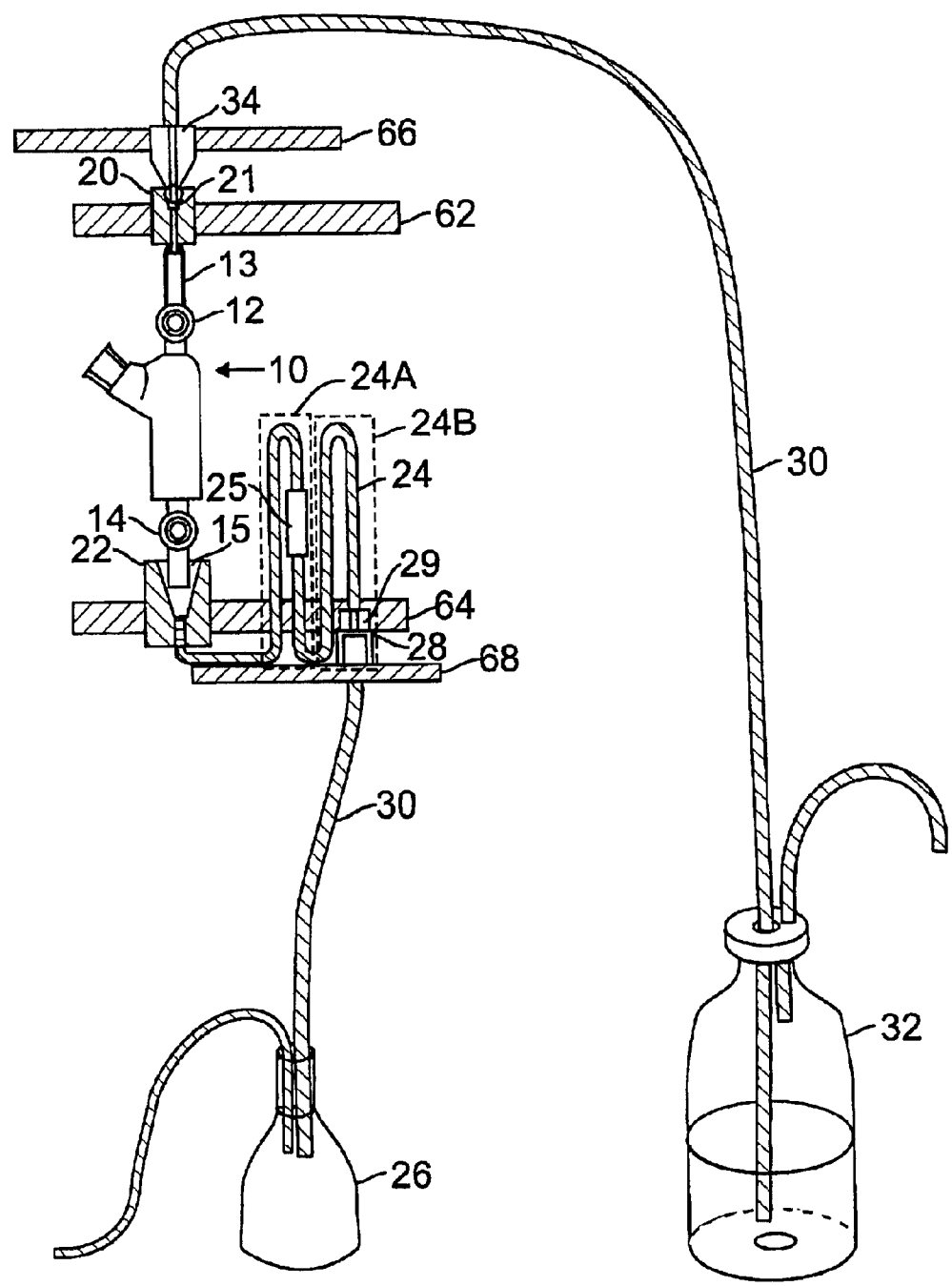
FIGS. 7A, 7B and 7C are illustrative views, respectively, of a reaction vessel with its fittings engaged, with its fittings disengaged, and with a U-valve apparatus opened, the U-valve being a U-valve apparatus employing a bidirectional check valve, in accordance with the present invention.

FIG. 7A illustrates aspects of a presently preferred embodiment of a reaction optimization tool in accordance with the present invention. In this embodiment, upper 62 and lower 64 carousel plates, respectively include the injection fittings 20 and evacuation fittings 22. As will be illustrated in greater detail in relation to the discussion of FIG. 8, an injection carousel 66 and a evacuation carousel 68 house the injection fittings 34 and evacuation fittings 28, respectively. In FIG. 7A, the injection 66 and evacuation carousels 68 are shown in the closed or clamped position, that is, with the injection 34 and evacuation 28 fittings engaged with the injection 21 and evacuation 23 ports, respectively. Although the evacuation fitting 28 and evacuation port 23 are engaged, they are engaged indirectly, through the fitting 29 and U-valve 24. The U-valve 24 includes first and second sections 24A and 24B. A bidirectional check valve 25, similar to the bidirectional check valve 214 of FIG. 2, is included in the U-valve 24.

Figure 7B:
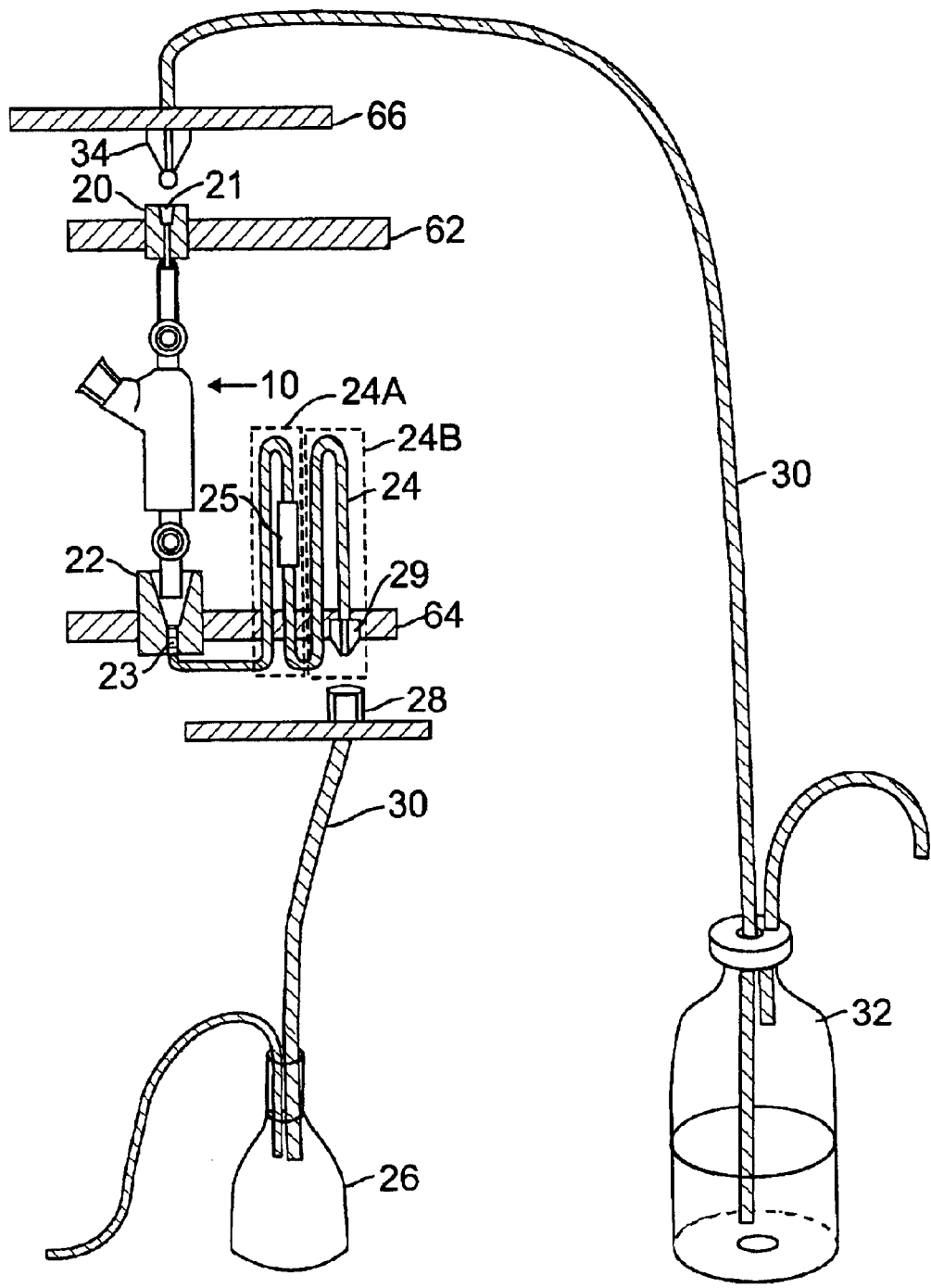
Figure 7C:
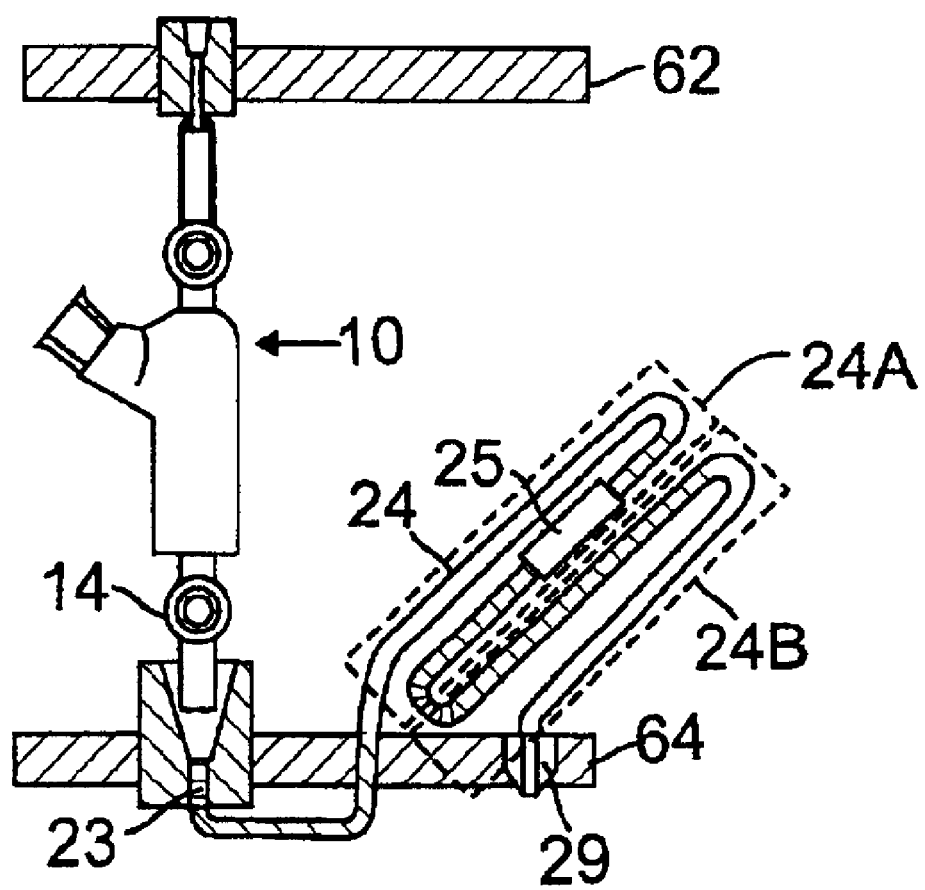

The injection carousel 66 and evacuation carousel 68 are shown separated in FIG. 7B, thus disengaging the respective injection fitting 34 and port 21 and evacuation fitting 29 and port 23. With the U-valve 24 in the illustrated vertical U-shaped position shown in FIG. 5, fluid normally will not flow from the vessel 10 into the U-valve 24 to a higher level than the fluid level within the vessel 10. If the liquid does flow into the U-valve past the fluid level within the vessel 10, due to use of small tubing IDs or sufficiently hot liquids, the check valve 25 will stop the flow of the liquid once liquid enters the second section 24B of the U-valve 24. Therefore, no fluids from within the vessel 10 will flow through the evacuating fitting 28 unless, as illustrated in FIG. 7C, the flexible tubing from which the U-valve 24 is made is bent over to a horizontal position so that sufficient head pressure is provided to force fluid through the valve 24, and negative pressure is applied. Bending the tubing of U-valve 24 may be accomplished by pulling on a cord attached to the valve, by pushing on a rod attached to the valve 24, by rotating U-valve 24 against a properly shaped camming surface, or the like. Applying a negative pressure to the U-valve 24 is necessary in order to open the float valve forming part of the bidirectional check valve 25, similar to the operation of the bidirectional check valve 214 of FIG. 2. To close the U-valve 24, the tubing is allowed or forced to return to its neutral, closed position illustrated in FIGS. 7A and 7B. Additionally, negative pressure is preferably released from the U-valve 24 in order to allow the bidirectional check valve to block liquid from flowing out of the U-valve 24.

If desired, a bidirectional check valve similar to the check valve 300 of FIG. 3 may be substituted for the check valve 25 shown in FIGS. 7A–7C. For an alternative configuration, the U-valve 24 and the check valve 25 shown in FIGS. 7A–7C may be replaced by a U-valve and flow interruption device similar to the U-valve 402 and flow interruption device 404 of FIG. 4.

Figure 8:
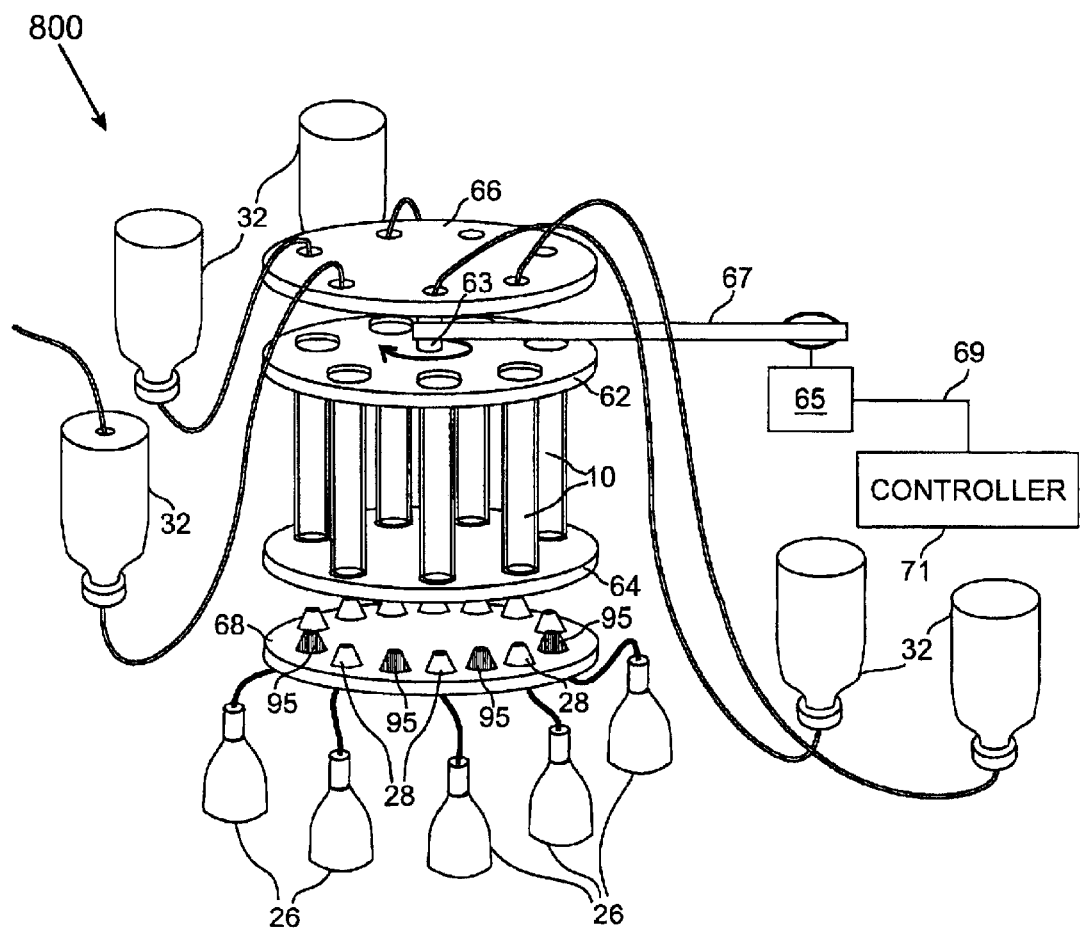
FIG. 8 is a perspective view of a carousel embodiment of a universal fluid exchanger suitably using a U-valve apparatus including a bidirectional check valve, in accordance with the present invention.

The perspective view of FIG. 8 illustrates a presently preferred universal solvent exchanger 800, with some components eliminated for the sake of clarity. The reaction vessels 10 (shown in simplified form) are arranged in a circular manner between the upper 62 and lower 64 carousel plates. One or more of the reaction vessels 10 may be advantageously employed with a U-valve including a check valve according to the present invention, as illustrated in FIG. 2, in order to provide control of liquid discharge and to prevent undesired liquid discharge. This carousel combination, including the fittings, which are not shown in this drawing, is supported by a framework in a conventional manner. A stepper motor 65 is attached to the combination through a timing belt 67 which rotates a shaft 63 which, in turn, causes the carousel combination to rotate through a desired angle subject to either manual or program control. It will be recognized that any suitable programmed computer and drive circuitry may be employed, and that while a stepper motor and timing belt are shown, rotation may be controllably caused utilizing any suitable motor, a Geneva mechanism, a rack and pinion drive, a pneumatic actuator or other known drive mechanisms.

In any case, the appropriate fittings and vessels are controllably rotated when the injection 66 and evacuation 68 plates are disengaged to the appropriate position as shown in FIG. 5. The plates 66 and 68 may be controlled by a clamping mechanism or actuator such as the actuator 36 of FIG. 5 or any of a variety of alternative actuators which may suitably control the positions of these plates. The stepper motor 65 of FIG. 8 is connected through electrical wires 69 to a controller 71, which is preferably a microprocessor based controller. The controller 71 controls the operation of motor 65 subject to stored program control. While rotation is principally employed to position the vessels for fluid exchange, it will be recognized that back and forth rotation of the carousel may be employed to cause mixing of the components in the vessels 10. The actuator may also be designed to vibrate or shake the carousel.

After appropriately aligning the vessels as discussed above, the injection 20 and evacuation ports 22 may be aligned and engaged with any of the respective injection 34 and evacuation 28 fittings located above and below them, respectively. A U-valve 24 including a check valve 25 according to the present invention may suitably be employed between one or more of the reaction vessels 10 and an associated evacuation fitting 28. The use of the U-valve 24 and the check valve 25 prevents inadvertent evacuation of liquid from the vessel 10. If desired, a bidirectional check valve similar to the check valve 300 may be substituted for the check valve 25. For an alternative configuration, the U-valve 24 and the check valve 25 may be replaced by a U-valve and flow interruption device similar to the U-valve 402 and flow interruption device 404 of FIG. 4. Blocking fittings 95 are shown interleaved with the evacuation fittings 28 on the evacuation carousel housing 68. Engagement with the blocking fittings 95 further ensures that no liquid will exit the bottom of the reaction vessels 10 when the contents of the vessels are agitated, for example, by rotating, vibrating or moving the upper and lower carousel plates 62 and 64 or when the vessels and their seals are under a pressure which could cause leakage. It will also be recognized that top blocking fittings may also suitably be employed for pressurized reactions and the like. In this way, liquid may be delivered to and evacuated from any vessel in any sequence desired, under program control. For example, chemical reagents may be added, solvents may be added and drained, washing solution may be flowed through the vessel, and a host of other liquids may be controllably flowed in and out of the vessel as desired. Thus, the present invention provides universal fluid exchange while avoiding complex tubing and control arrangements and also while avoiding cross contamination.

Figure 9:
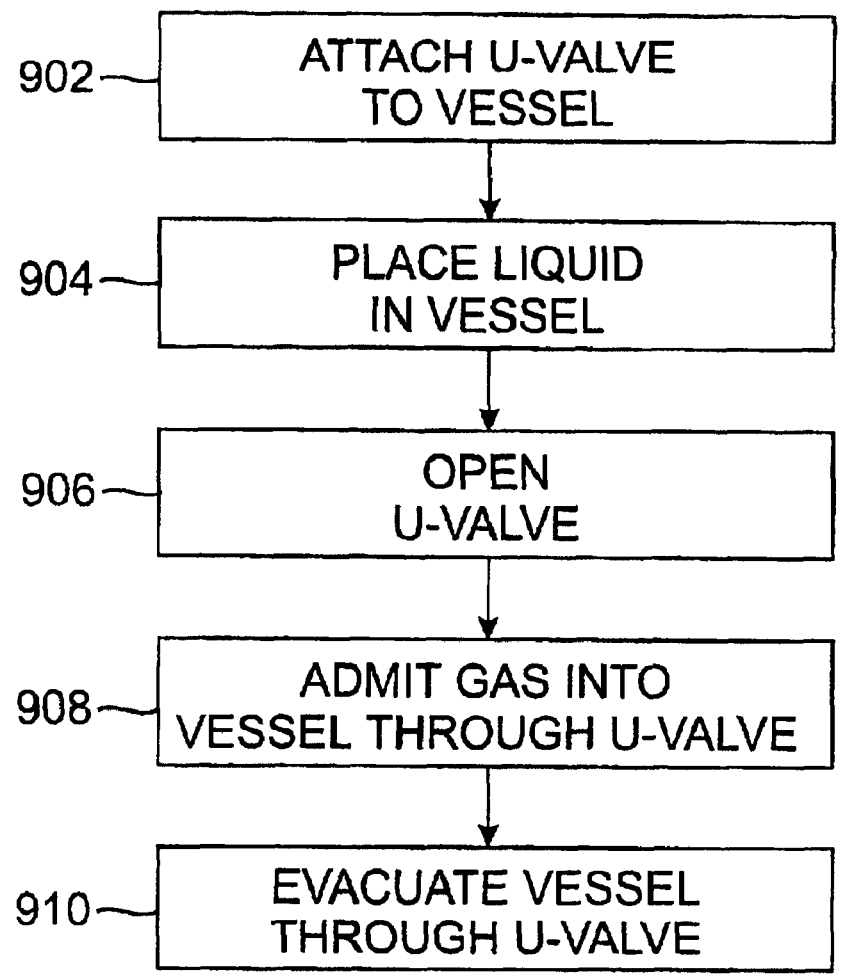
FIG. 9 illustrates a method for control of liquid flow from a U-valve according to the present invention.

FIG. 9 is a flowchart illustrating the steps of a method for control of liquid flow 900 according to the present invention. At step 902, a U-valve having first and second sections containing first and second apexes, similar to the U-valve 212 of FIG. 2, and containing a bi-directional check valve 214 similar to the bi-directional check valve 214 of FIG. 2, is connected to a vessel. The bidirectional check valve 214 includes a first channel containing a ball valve and a second channel containing a float valve. At step 904, liquid is placed into the vessel. At step 906, the apex of each of the first and second sections of the U-valve is lowered. Liquid flows into the U-valve, with any liquid which does not stop upon reaching the level of liquid in the vessel being blocked by the bi-directional valve. At step 908, gas is introduced into the first channel. The ball valve allows the gas to pass through the bidirectional valve and into the vessel, purging or agitating the liquid in the vessel, as controlled by the gas pressure. At step 910, a negative pressure is applied to the U-valve, opening the float valve and allowing the vessel to be evacuated through the U-valve. Steps 906–910 need not be executed in sequence; instead, the steps are executed in the order desired. For example, the agitation step might be skipped, or alternatively executed multiple times.

The foregoing description of specific embodiments of the invention has been presented for the purposes of illustration and description. It is not intended to be exhaustive or to limit the invention to the precise forms disclosed, and many modifications and variations are possible in light of the above teachings. For example, while the present invention has been disclosed principally in the combinatorial chemistry context, it will be recognized that its teachings may be generally applicable to parallel synthesis, tagging and tag washing, solvent exchangers, bead washers and the like.

I claim:

1. A flow-interrupting U-valve apparatus for connection to a discharge port of a vessel, for preventing inadvertent liquid flow from the vessel through the U-valve, comprising:
  a U-valve;
  a flow-interruption device within the U-valve, the flow-interruption device comprising:
    a sealed chamber;
    an inlet connected to a portion of the U-valve connected to the discharge port of the vessel, the inlet allowing entry of liquid into the chamber; and
    an outlet connected to a section of the U-valve adapted to allow discharge of the liquid, the outlet being separate from the inlet in order to interrupt flow of liquid entering the chamber from flow of liquid exiting the chamber.

2. The flow-interrupting U-valve apparatus of claim 1 wherein the flow-interruption device allows liquid to flow into the chamber until the level of liquid in the chamber reaches the level of liquid in the vessel.

3. The flow-interrupting U-valve apparatus of claim 1 wherein the flow-interruption device prevents siphoning of the liquid.

4. The flow-interrupting U-valve apparatus of claim 1 wherein the flow-interruption device allows purging of the vessel utilizing negative pressure.

5. The flow-interrupting U-valve apparatus of claim 1 wherein the flow-interruption device allows agitation of liquid within the vessel utilizing a passage of gas into the vessel.

6. The flow-interrupting U-valve apparatus of claim 1 wherein the flow-interruption device allows the vessel to be evacuated utilizing suction applied to the outlet.

7. A chemical synthesis reaction tool, comprising:
  a reaction vessel;
  a reaction vessel support disposed to hold the reaction vessel in a preferred orientation,
  an injection port, including a pressure seal, situated to provide access to said reaction vessel for the injection of liquids into said reaction vessel;
  an evacuation port, including a pressure seal, situated to provide access to said reaction vessel for the evacuation of fluids from said reaction vessel;
  injection and evacuation fittings formed to matingly engage said respective injection and evacuation ports and to thereby enable the delivery of fluids to the reaction vessel and the evacuation of fluids from said reaction vessel;
  a U-valve formed of flexible tubing and connected to regulate the flow of liquids from said evacuation through fitting;
  a flow-interruption device within the U-valve, the flow-interruption device comprising:
    a sealed chamber;
    an inlet connected to a portion of the U-valve connected to the discharge port of the vessel, the inlet allowing entry of liquid into the chamber; and
    an outlet connected to a section of the U-valve adapted to allow discharge of the liquid, the outlet being separate from the inlet in order to interrupt flow of liquid entering the chamber from flow of liquid exiting the chamber.

8. The flow-interrupting U-valve apparatus of claim 7 wherein the flow-interruption device allows liquid to flow into the chamber until the level of liquid in the chamber reaches the level of liquid in the vessel.

9. The flow-interrupting U-valve apparatus of claim 7 wherein the flow-interruption device prevents siphoning of the liquid.

10. The flow-interrupting U-valve apparatus of claim 7 wherein the flow-interruption device allows purging of the vessel utilizing negative pressure.

11. The flow-interrupting U-valve apparatus of claim 7 wherein the flow-interruption device allows agitation of liquid within the vessel utilizing a passage of gas into the vessel.

12. The flow-interrupting U-valve apparatus of claim 7 wherein the flow-interruption device allows the vessel to be evacuated utilizing suction applied to the outlet.

13. A universal fluid exchanger comprising:
  a reaction vessel;
  a reaction vessel support disposed to hold the reaction vessel in a preferred orientation;

an injection port, including a pressure seal, situated to provide access to said reaction vessel for the injection of liquids into said reaction vessel;

an evacuation port, including a pressure seal, situated to provide access to said reaction vessel for the evacuation of fluids from said reaction vessel;

injection and evacuation fittings formed to matingly engage said respective injection and evacuation ports and to thereby enable the delivery of fluids to the reaction vessel and the evacuation of fluids from said reaction vessel;

an actuator for controlling selectively aligning the injection and evacuation ports and the injection and evacuation fittings, respectively; and a U-valve formed of flexible tubing and connected to regulate the flow of liquids from said evacuation through fitting;

a flow-interruption device within the U-valve, the flow-interruption device comprising:
  a sealed chamber;
  an inlet connected to a portion of the U-valve connected to the discharge port of the vessel, the inlet allowing entry of liquid into the chamber; and
  an outlet connected to a section of the U-valve adapted to allow discharge of the liquid, the outlet being separate from the inlet in order to interrupt flow of liquid entering the chamber from flow of liquid exiting the chamber.

14. The flow-interrupting U-valve apparatus of claim 13 wherein the flow-interruption device allows liquid to flow into the chamber until the level of liquid in the chamber reaches the level of liquid in the vessel.

15. The flow-interrupting U-valve apparatus of claim 13 wherein the flow-interruption device prevents siphoning of the liquid.

16. The flow-interrupting U-valve apparatus of claim 13 wherein the flow-interruption device allows purging of the vessel utilizing negative pressure.

17. The flow-interrupting U-valve apparatus of claim 13 wherein the flow-interruption device allows agitation of liquid within the vessel utilizing a passage of gas into the vessel.

18. The flow-interrupting U-valve apparatus of claim 13 wherein the flow-interruption device allows the vessel to be evacuated utilizing suction applied to the outlet.

\* \* \* \* \*